United States Patent
Soulillou et al.

(10) Patent No.: US 11,084,871 B2
(45) Date of Patent: Aug. 10, 2021

(54) COMPOSITION WITH REDUCED IMMUNOGENICITY

(71) Applicant: INSERM (Institut National de la Sante et de la Recherche Medicale), Paris (FR)

(72) Inventors: Jean-Paul Soulillou, Nantes (FR); Magali Giral, Carquefou (FR); Gregoire Couvrat-Desvergnes, Nantes (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 0 days.

(21) Appl. No.: 14/785,138

(22) PCT Filed: Apr. 17, 2014

(86) PCT No.: PCT/IB2014/060813
§ 371 (c)(1),
(2) Date: Oct. 16, 2015

(87) PCT Pub. No.: WO2014/170867
PCT Pub. Date: Oct. 23, 2014

(65) Prior Publication Data
US 2016/0075770 A1    Mar. 17, 2016

(30) Foreign Application Priority Data
Apr. 18, 2013 (EP) .................................... 13305507

(51) Int. Cl.
*A61K 39/00* (2006.01)
*A61K 39/395* (2006.01)
*C07K 16/18* (2006.01)

(52) U.S. Cl.
CPC ........ *C07K 16/18* (2013.01); *A61K 39/39516* (2013.01); *A61K 39/00* (2013.01); *A61K 2039/505* (2013.01); *C07K 2317/14* (2013.01); *C07K 2317/21* (2013.01); *C07K 2317/40* (2013.01)

(58) Field of Classification Search
None
See application file for complete search history.

(56) References Cited

U.S. PATENT DOCUMENTS

2017/0240616 A1* 8/2017 Duvaux ............... C12N 9/0071

FOREIGN PATENT DOCUMENTS

| EP | 0388151 A1 | 9/1990 |
| WO | 03097812 A2 | 11/2003 |

OTHER PUBLICATIONS

Gaber et al., Drugs 70:691-732 (2010).*
"Ungulate", Merriam-Webster.com, available online at https://www.merriam-webster.com/dictionary/ungulate, 12 pages (accessed on Nov. 2, 2017) (Year: 2017).*
Lutz et al., "Double Knockout Pigs Deficient in N-Glycolylneuraminic Acid and Galactose [alpha]-1, 3 Galactose Reduce the Humoral Barrier to Xenotransplantation" Xenotransplantation, Jan. 5, 2013, vol. 20, No. 1, p. 27-35.
Darius Ghaderi et al: "Production platform for biotherapeutic glycoproteins. Occurrence, impact, and challenges of non-human sialylation", Biotechnology and Genetic Reviews, vol. 28, No. 1, pp. 147-176, Jan. 1, 2012.
Guillaume Bussone et al: "Identification of target antigens of self-reactive IgG in intravenouos immunoglobulin preparations", Proteomics, vol. 9, No. 8, pp. 2253-2262, Apr. 1, 2009.
European Patent Office, Office Action, dated Oct. 6, 2017.
Qian et al.; "Tumor associated antigen recognition by autologous serum in patients with breast cancer"; International Journal of Molecular Medicine, vol. 15, 2001, pp. 137-144.
Sharon et al.; "Recombinant Polyclonal Antibodies for Cancer Therapy"; Journal of Cellular Biochemistry, vol. 96, 2005, pp. 305-313.
Ghaderi et al.; "Implications of the presence of N-glycolylneuraminic acid in recombinant therapeutic glycoproteins"; Nature Biotechnology, vol. 28, No. 8, Aug. 2010, pp. 863-867.
Sandhu et al.; "Is Thymoglobulin or Rituximab the Cause of This Serum Sickness? A Case Report of Serum Sickness Dilemma and Literature Review"; Case Reports in Medicine, vol. 2012, Article ID 234515, pp. 1-7.
European Patent Office, Office Action, dated Oct. 23, 2018.
Jung et al.; « Bypassing glycosylation : engineering aglycosylated full-length IgG antibodies for human therapy » ; Current opinion in Biotechnology ; 2011.

* cited by examiner

*Primary Examiner* — Thea D' Ambrosio
(74) *Attorney, Agent, or Firm* — W & C IP

(57) ABSTRACT

The present invention relates to a composition comprising polyclonal antibodies directed against human cells, wherein the said polyclonal antibodies are devoid of a first antigenic determinant selected in a group comprising (i) N-glycolneuraminic acid (Neu5Gc) and (ii) α-1,3-galactose and its use as a medicament.

8 Claims, 5 Drawing Sheets

COMPOSITION WITH REDUCED IMMUNOGENICITY

FIELD OF THE INVENTION

The present invention relates to the field of immunology and more particularly to Anti-Lymphocyte Sera (ALS) and Anti-Thymocyte Globulin (ATG) and their use in human medicine.

DESCRIPTION OF RELATED ART

It is known in the art that allograft rejection involves mainly activated human T cells which, in contact with cellular antigens of the donor, were transformed into deleterious effectors lymphocytes that destroy the graft's cells.

To ensure successful organ transplantation and a long-term survival of grafts, it has been proposed to counteract the noxious effect of T cells of grafted patients with respect to the graft by administration of Anti-Lymphocyte Serum (ALS) and Anti-Thymocyte Globulin (ATG) (Mohty M et al., Best Pract. Res. Clin. Haematol., 2010 June; 23 (2): 275-82).

Also, according to a distinct therapeutic strategy, a reduction of the noxious effect of T cells in grafted patients has been obtained by using monoclonal antibodies directed to specific membrane-borne antigens. It is worth mentioning the use of basiliximab, which is a monoclonal antibody directed against the alpha subunit (CD25) of the interleukin-2 receptor (IL-2R) on activated lymphocytes. May be also cited the use of Alemtuzumab (marketed as Campath, MabCampath or Campath-1H and currently under further development as Lemtrada) which is a monoclonal antibody directed against the cell surface glycoprotein (CD 52) present on the surface of mature lymphocytes.

Compared notably to monoclonal antibodies such as basiliximab or Alemtuzumab, ALS and ATG inhibit a plurality of distinct receptors, thereby causing a marked depletion of T-lymphocytes (S Louis et al., Transplantation, 2007, vol. 83: 712-721).

Thus, it is known in the art that ALS and ATG may reduce the incidence of acute rejection, may also treat acute rejection episodes as well as improve graft survival (Gaber A O et al., Drugs. 2010 Apr. 16; 70 (6): 691-732; Lawen J G et al., Transplantation 2003, 75: 37-43; Lee B M et al., Transplant. Proc. 2006, 38: 2025-2028; Gaber A O et al., Drugs. 2010 Apr. 16; 70 (6): 691-732; Mohty M et al., Best Pract. Res. Clin. Haematol., 2010 June; 23 (2): 275-82).

For example, to date, ALS and ATG are the most popular treatment of induction for kidney.

ALS and ATG are infusions of non-human animals-derived polyclonal antibodies against human cells, in particular human T cells. More particularly, ALS and ATG are serum polyclonal antibodies obtained by immunization of non-human animals, such as rabbits and horses, using xenogeneic cells (especially lymphocytes), in particular human lymphocytes, human thymocytes or human immortalized cell line in the case of the preparation of ALS and ATG intended to be used by humans.

ALS and ATG have an immuno-suppressant effect which has been demonstrated in humans, and are thus used to prevent and/or treat the graft rejection, including in the prevention and/or the treatment of acute rejection in organ transplantation.

ALS and ATG are also used in the prevention and/or treatment of aplastic anemia and also of graft-versus-host disease (GVHD) (Norbert Frickhofen et al., N Engl J Med 1991, 324: 1297-1304; Kaya B et al., J. Clin. Pathol. 58 (9): 994-5; Stein R S et al., Am J Med Sci. 1994 December; 308(6): 338-43; Bacigalupo A et al., Blood 98 (10): 2942-7; Bacigalupo A et al., Biology of Blood and Marrow Transplantation 12 (5): 560-5).

However, conventional ALS and ATG are known to be associated with unwanted adverse effects (T U et al., Chin. Med. J., 2012, 125 (9): 1664-1666; WANG et al., Chin. Med. J., 2012, 125(6): 1135-1140).

In particular, conventional ALS and ATG are known to be associated with cytokine release syndrome in the short term and an increased risk of post-transplant lymphoproliferative disorder in the long term.

Moreover, despite they are currently administered with other immunosuppressive drugs, ALS and ATG remain strongly immunogenic and are responsible for the generation of immune complex (IC) related diseases including severe IC manifestations such as skin rashes, fever, etc.

In this regard, the inventors show for the first time that the serum sickness occurrence is an independent variable linked to the late graft loss. Moreover, the inventors observe for the first time a statistical significant association between serum sickness and an increase in anti-Neu5Gc IgG antibodies years after transplantation (see herein after example 4).

Thus, there remains a need for the provision of compositions endowed with reduce adverse effects, including compositions which are improved or alternative as regards the conventional ALS or ATG compositions, and which are significantly less immunogenic, when compared to the conventional ALS or ATG, and which ideally do not involve the manifestation of IC related diseases.

SUMMARY OF THE INVENTION

According to a first of its aspects, the invention relates to a composition comprising polyclonal antibodies directed against human cells, wherein the said polyclonal antibodies are devoid of a first antigenic determinant selected in a group comprising (i) N-glycolneuraminic acid (Neu5Gc) and (ii) α-1,3-galactose.

According to another of its aspect, the invention relates to a method for producing a composition of polyclonal antibodies according to the invention comprising the steps of:

a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional α-(1,3)-galactosyltransferase;

b) immunizing the said genetically altered non-human mammal against human cells; and c) collecting the antibodies contained in a body fluid of the said genetically altered non-human mammal of step b).

As it is known in the art, antibodies against human cells may be easily obtained by immunizing a non-human mammal, which includes pigs, horses or rabbits, by administration of an immunogenic composition comprising target human cells.

This is specifically illustrated by the preparation of compositions termed "ALS" and "ATG" which are obtained by immunizing non-human mammals with human cells, namely human lymphocytes and human thymocytes, respectively.

Then, polyclonal antibodies against any kind of human cells may be obtained by immunizing a non-human mammal with the said human cells.

This includes polyclonal antibodies of therapeutic interest, which antibodies are directed against cells, the presence of which in a human organism is indesirable.

This includes polyclonal antibodies directed against cells exerting deleterious effects to the human organism, such as lymphocytes which are noxious towards a tissue graft or an organ graft or such as cells having deregulated proliferating properties like malignant cells (tumor cells or cancer cells).

Therefore, the said human cells may be preferably selected in a group comprising human lymphocytes, human thymocytes and human cancer cells, more particularly in a group comprising human lymphocytes and human thymocytes.

The present invention also contemplates the use of a genetically altered non-human mammal lacking a first gene selected from the group comprising (i) a gene encoding a functional cytidine-5'-monophosphate N-acetyl neuraminic acid hydrolase (CMAH) and (ii) a gene encoding a functional α-(1,3)-galactosyltransferase, for producing a composition comprising polyclonal antibodies directed against human cells.

The implementation of a such genetically altered non-human mammal is further advantageous in that said genetically altered non-human mammal only develops minimal amount of anti NeuGc antibodies on unmodified diet, as displayed in example 3 and FIG. 5. Thus, this exempts of a step of immune-absorption of the serum of said genetically altered non-human mammal before its injection in a human patient.

According to another of its aspects, the invention relates to a method for inducing an immunosuppression state in an individual in need thereof, the said method comprising a step of administering to the said individual a composition according to the invention.

According to another of its aspects, the invention relates to a composition according to the invention for its use as a medicament.

The present invention also pertains to a composition as described above for its use for preventing and/or treating a disorder selected in a group comprising a graft rejection, aplastic anemia, a graft-versus-host disease, a severe autoimmune disease and a malignant cells related disease.

According to yet another of its aspects, the invention relates to a composition as described above for its use for preventing and/or treating a graft rejection, especially a renal graft rejection.

The present invention also contemplates a composition as described above for its use for preventing post-transplant IC related diseases, in particular serum sickness, skin rashes or fever.

In some embodiments, the composition comprising polyclonal antibodies is selected in a group comprising an anti-Lymphocyte Serum (ALS) and an Anti-Thymocyte Globulin serum (ATG).

BRIEF DESCRIPTION OF THE DRAWINGS

FIGS. 1 and 2 relate to multi-centric and mono-centric DIVAT cohort respectively but FIG. 3, which has been used for the statistical study, relates to a more homogeneous mono-centric cohort (DIVAT, Nantes), as herein after shown in tables A to C.

DETAILED DESCRIPTION OF THE INVENTION

1. Definitions

Figure 1:
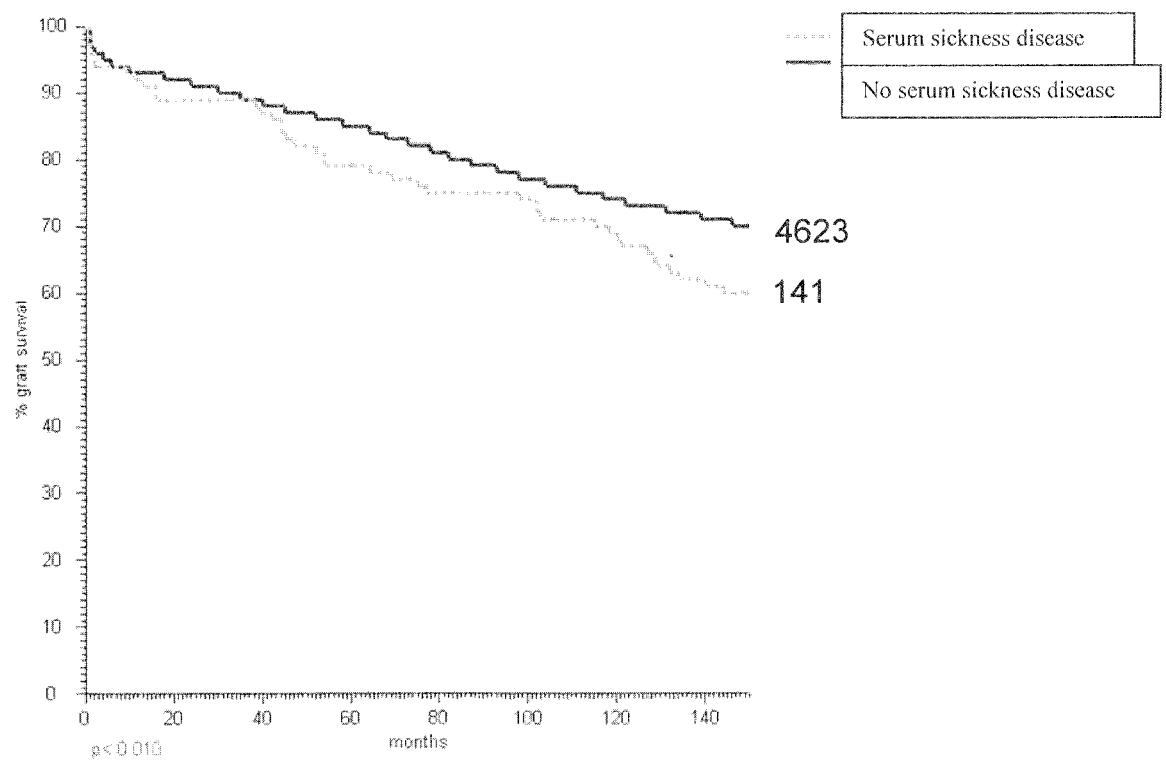
FIG. 1: illustrates a graph of collected data regarding, from patients (multi-centric cohort of the DIVAT databank, Nantes Transplantation Institute, Nantes) having received at least one kidney graft and an induction treatment with ALS or ATG and in this regard having developed immune complex (IC) related diseases, the proportion who display a serum sickness and the related adverse effects with respect to the long term graft survival (Abscissa: duration (in months); Ordinate: % of graft survival).
Figure 2:
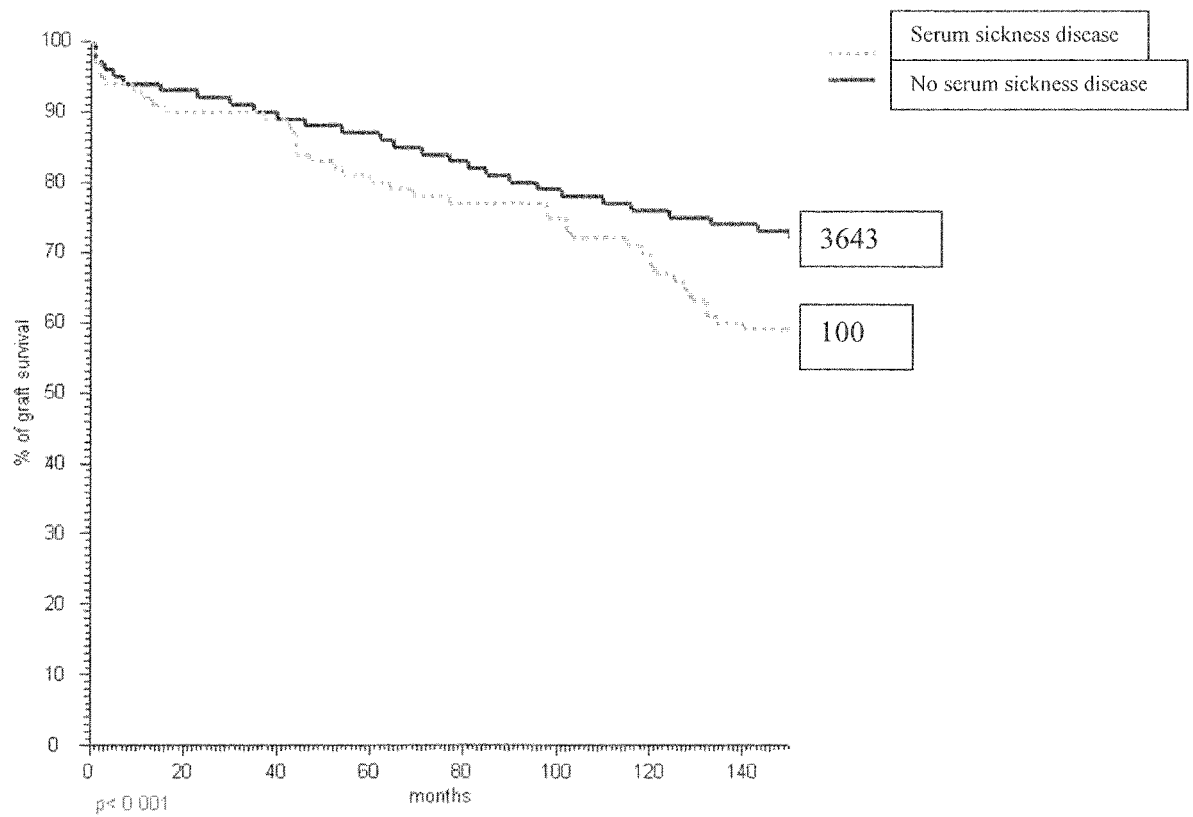
FIG. 2: illustrates a graph of collected data regarding, from patients (mono-centric cohort of the DIVAT databank, Nantes Transplantation Institute, Nantes) having received a kidney graft and a treatment with ALS or ATG and in this regard having developed immune complex (IC) related diseases, the proportion who display a serum sickness and the related adverse effects with respect to the long term graft survival (Abscissa: duration (in months); Ordinate: % of graft survival).

In order that the invention may be more completely understood, several definitions are set forth below. Such definitions are meant to encompass grammatical equivalents.

The term "antibody" is used herein in the broadest sense. "Antibody" refers to any polypeptide which at least comprises (i) a Fc region and (ii) a binding polypeptide domain derived from a variable region of an immunoglobulin. Antibodies thus include, but are not limited to, full-length immunoglobulins, antibodies, antibody conjugates and fragments of each respectively. The terms "antibody" and "immunoglobulin" may be used interchangeably herein.

The term "antibody" encompasses a polypeptide as above-mentioned which further comprises at least one sugar moiety distinct from the antigenic determinant selected in a group comprising (i) N-glycolneuraminic acid (Neu5Gc) and/or (ii) α-1,3-galactose.

By "polyclonal antibodies" as used herein is meant a mixture of antibodies recognizing different epitopes of a given antigen. Polyclonal antibodies encompass those which are contained in, or alternatively which are derived from, body fluids, especially serum or plasma from a mammal organism.

In the case of human immunoglobulins, light chains are classified as kappa and lambda light chains. Heavy chains are classified as mu, delta, gamma, alpha, or epsilon, and define the antibody's isotype as IgM, IgD, IgG, IgA, and IgE, respectively.

By "IgG" as used herein is meant a polypeptide belonging to the class of antibodies that are substantially encoded by a recognized immunoglobulin gamma gene. In humans, IgG comprises the subclasses or isotypes IgG1, IgG2, IgG3, and IgG4. In mice, IgG comprises IgG1, IgG2a, IgG2b, IgG3. Full-length IgGs consist of two identical pairs of two immunoglobulin chains, each pair having one light and one heavy chain, each light chain comprising immunoglobulin domains VL and CL, and each heavy chain comprising immunoglobulin domains VH, Cγ1 (also called CH1), Cγ2 (also called CH2), and Cγ3 (also called CH3).

As used herein, "Antibody-dependent cell-mediated toxicity" (or ADCC) refers to a mechanism of cell-mediated immunity whereby an effector cell of the immune system actively lyses a target cell that has been bound by specific antibodies. ADCC is mostly mediated by NK cells but also by other immune cells such as neutrophils and eosinophils. Typically, ADCC results from the activation of NK cells. The activation of NK cells involves the binding of their Fc receptors to the Fc region of IgG bound to antigens present on the surface of target cells. Such interactions induce the release by NK cells of cytokines and cytotoxic granules. To assess the capacity of an antibody to induce ADCC, an assay, as described in de Romeuf et al. Br J Haematol. 2008 March; 140(6):635-43, may be performed.

By "antigenic determinant" (or epitope), as applied herein to non-human mammal polyclonal antibodies, as used herein is meant a structural component of an antigenic molecule, which includes an antigenic protein and an antigenic carbohydrate, responsible for its specific interaction with antibody molecules elicited by the same or related antigen. By extension, the term "antigenic determinant", as applied herein to non-human mammal polyclonal antibodies is also used collectively herein for an antigenic molecule comprising a plurality of epitopes susceptible to be recognized by antibody molecules elicited by the same or related antigen. Illustratively, the antigenic molecule N-glycolneuraminic acid (Neu5Gc) may be called herein an "antigenic determinant", although the said antigenic molecule may contain more than one epitope recognized by antibodies elicited with Neu5Gc or with Neu5Gc containing molecules.

"Thymocytes" are hematopoietic progenitor cells present in the thymus. Thymopoiesis is the process in the thymus by which thymocytes differentiate into mature T lymphocytes.

"T cells" or "T lymphocytes" belong to a group of white blood cells known as lymphocytes, and play a central role in cell-mediated immunity. They can be distinguished from other lymphocytes, such as B cells and natural killer cells (NK cells), by the presence of a T-cell receptor (TCR) on the cell surface. They are called T cells because they mature in the thymus.

"B cells" or "B lymphocytes" also belong to a group of white blood cells known as lymphocytes, making them a vital part of the immune system—specifically the humoral immunity branch of the adaptive immune system. B cells can be distinguished from other lymphocytes, such as T cells and natural killer cells (NK cells), by the presence of a protein on the B cell's outer surface known as a B cell receptor (BCR). This specialized receptor protein allows a B cell to bind to a specific antigen. The main functions of B cells are to make antibodies against antigens, to perform the role of antigen-presenting cells (APCs), and to develop into memory B cells after activation by antigen interaction.

In blood, the "serum" is the plasma-derived component wherein cells (white blood cells as well as red blood cells) and clotting factors have been removed. Serum includes all proteins not used in blood clotting (coagulation) and all the electrolytes, antibodies, antigens, hormones, and any eventually also exogenous substances (e.g. drugs and microorganisms).

"Anti-Lymphocyte Sera" (or ALS) and "Anti-Thymocyte Globulin" (or ATG) are, as above-mentioned, infusions of non-human animals-derived polyclonal antibodies against human lymphocytes and human thymocytes, respectively.

By "conventional serum" and in particular by "conventional anti-Lymphocyte Serum (ALS)" and "conventional Anti-Thymocyte Globulin serum (ATG)" (or "known serum, known ATG or known ALS"), as used herein is meant serum for which the polyclonal antibodies that are comprised therein are not devoid of an antigenic determinant selected in a group comprising (i) N-glycolneuraminic acid (Neu5Gc) and/or (ii) α-1,3-galactose. In this regard, it may be notably cited the products commercialized under the name Thymoglobulin by the company Genzyme, or the name Atgam by the company Pfizer.

The terms "malignant cells", "cancer cells" and "tumor cells" may be used interchangeably herein. As used herein, "tumor cells" refer to cells which hyperproliferate autonomously in vivo. Examples of tumor cells include cells included in (1) sarcomas such as osteosarcoma and soft tissue sarcoma, (2) carcinomas such as carcinoma of the breast, carcinoma of the lung, carcinoma of the bladder, carcinoma of the thyroid gland, carcinoma of the prostate, carcinoma of the colon, colorectal carcinoma, carcinoma of the pancreas, carcinoma of the stomach, carcinoma of the liver, carcinoma of the uterus, carcinoma of the cervix and carcinoma of the ovary, (3) lymphomas such as Hodgkin lymphoma and non-Hodgkin lymphoma, (4) neuroblastomas, (5) melanomas, (6) myelomas, (7) Wilms tumors, (8) leukemias such as acute myelocytic leukemia (AML), chronic myelocytic leukemia (CIVIL), acute lymphocytic leukemia (ALL) and chronic lymphocytic leukemia (CLL), (9) gliomas, and (10) retinoblastomas.

As used herein, the terms "cancer" means the uncontrolled, abnormal growth of cells and includes within its scope all the well known diseases that are caused by the uncontrolled and abnormal growth of cells. Non-limiting examples of common cancers include bladder cancer, breast cancer, ovarian cancer and gastric cancer, cervical cancer, colon cancer, endometrial cancer, head and neck cancer, lung cancer, melanoma, multiple myeloma, leukemia (e.g. myeloid, lymphocytic, myelocytic and lymphoblastic leukemias), non-hodgkin's lymphoma, prostate cancer, rectal cancer, malignant melanomas, and in particular pancreatic cancer.

As used herein, the term "autoimmune disease" means a disease resulting from an immune response against a self tissue or tissue component, including both self antibody responses and cell-mediated responses.

The term autoimmune disease, as used herein, encompasses organ-specific autoimmune diseases, in which an autoimmune response is directed against a single tissue, such as type I diabetes mellitus (T1 D), Crohn's disease, ulcerative colitis, myasthenia gravis, vitiligo, Graves' disease, Hashimoto's disease, Addison's disease and autoimmune gastritis and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include pernicious anemia including some of autoimmune gastritis, primary biliary cirrhosis, autoimmune thrombocytopenia, Sjogren's syndrome, multiple sclerosis and psoriasis. One skilled in the art understands that the methods of the invention can be applied to these or other autoimmune diseases, as desired. Non-limiting examples of severe auto-immune disease also include thrombocytopenia such as the idiopathic thrombocytopenic purpura (ITP), birdshot retinochoroiditis type, Guillain-Barré syndrome (GBS), multifocal motor neuropathy or Kawasaki disease or lympho-mucocutaneous syndrome, autoimmune thyroiditis, or ankylosing spondylitis.

2. Composition According to the Invention

It has been found according to the invention that, in a population of grafted patients who have received a treatment with ALS or ATG, the graft survival time mainly depends on the occurrence of IC related diseases such as serum sickness disease in these patients undergoing generation of immune complex (IC). More precisely, the inventors have found that those ALS-treated or ATG-treated patients experiencing an IC related disease, and especially serum sickness, have a highly significant reduced graft survival time and a poor long-term outcome, the latter being comparable to that observed in graft rejection caused by five versus one HLA incompatibilities.

With the view of overcoming the drawbacks of the conventional ALS or ATG, the inventors have conceived compositions comprising polyclonal antibodies having reduced immunogenic properties in human individuals, and thus having reduced ability to induce Immunogenic Complex (IC) in human and consequently, a reduced ability to induce IC related diseases such as serum sickness.

This invention primarily relates to a composition comprising polyclonal antibodies directed against human cells, wherein the said polyclonal antibodies are devoid of a first antigenic determinant selected in a group comprising (i) N-glycolneuraminic acid (Neu5Gc) and (ii) α-1,3-galactose.

According to a particular embodiment, the composition according to the invention may be further devoid of a second antigenic determinant which is distinct from the first antigenic determinant and wherein the said second antigenic determinant is selected in a group comprising (i) N-glycolneuraminic acid (Neu5Gc) and (ii) α-1,3-galactose.

The polyclonal antibodies contained in a composition of polyclonal antibodies according to the invention are believed to possess reduced immunogenic properties in human as compared with the compositions of polyclonal antibodies that are currently used in the art under the form of ALS and ATG.

It is known in the art that Neu5Gc is immunogenic in humans (Noguchi A. et al., J. Biochem. Tokyo (1995), 117(1): 59-62). Further, it is known that patients developing severe Immune Complex (IC) following infusion of animals immunoglobulins mount antibodies which are mostly developed against the Neu5Gc epitope (Merrick J M et al., Int. Allergy Appl. Immunol., 1978, Vol. 57: 477-480; Aggarwal S. et al., Nat Biotechnol. 2008; 26:1227-1233; Arnold J N et al., Annu Rev Immunol. 2007; 25:21-50; Durocher Y et al., Curr Opin Biotechnol. 2009; 20:700-707; Higgins E et al., Glycoconj. J. 2009).

It is also known in the art that the enzyme α-1,3-galactosyltransferase (α-1,3GT or GGTA1) synthesizes α-1,3-galactose (α-1,3Gal) epitopes (Galα-1,3Galβ1,4G1cNAc-R), which are the major xenoantigens causing hyperacute rejection in pig-to-human xenotransplantation.

Consequently, a composition containing polyclonal antibodies devoid of (i) N-glycolneuraminic acid (Neu5Gc) and/or (ii) α-1,3-galactose antigenic determinants, because these polyclonal antibodies are less immunogenic than the polyclonal antibodies that are contained in conventional ALS and ATG, possesses reduced immunogenic. Then, such a composition containing polyclonal antibodies according to the invention is believed to possess reduced properties in raising the various adverse effects that are induced after administration of conventional ALS or ATG products, which include the induction of severe IC diseases, including serum sickness, cytokine release syndrome and of post-transplant lymphoproliferative disorder.

Thus, a composition containing polyclonal antibodies according to the invention is believed to reduce the risk of occurrence of the conventional ALS-induced or of the conventional ATG-induced adverse effects, each of these adverse effects contributing to a decreased long term graft survival in humans, as shown herein.

According to the inventors knowledge, no ALS or ATG devoid of an antigenic determinant selected in a group comprising (i) Neu5Gc and/or (ii) α-1,3-galactose, is known in the art, more particularly for the use disclosed in the present specification.

In this regard, a composition according to the invention is particularly advantageous in that it precisely allows overcoming the above-mentioned undesirable effects caused by the conventional ALS and ATG in that it preserves its immune-modulating properties against human T cells and/or B cells while being less toxic at a systemic level of the human organism.

In other words, a composition according to the invention is significantly less immunogenic and thus, the occurrence of immune complex (IC) related diseases, and especially the serum sickness, observed with conventional ALS or ATG is expected to be significantly reduced.

An associated advantage to a composition according to the invention is that it allows improving significantly the long term graft survival.

In addition, it is known in the art that N-glycosylation of antibodies plays a crucial role in the modulation of their effectors properties, especially of their pro- or anti-inflammatory properties.

Thus, it has been identified that the sialylation is the addition of N-acetylneuraminic acid, also called Neu5Ac, NANA, N-acetylsialic or sialic acid, on galactose residues of N-glycans of the crystallizable fragment (Fc) of antibodies.

The sialylation imparts to antibodies particularly interesting anti-inflammatory properties (Dimitrov et al.; Nephrol. Dial. Transplant., 2007.22: 1301 and WO 2007/117505).

Therefore, according to the embodiment wherein polyclonal antibodies according to the present invention are devoid of at least the antigenic determinant N-glycolneuraminic acid (Neu5Gc), said polyclonal antibodies are further advantageous in that they display, by allowing a more physiological access to Fc Gamma receptor, an increased affinity for FcγR and thus, an increased ADCC with respect to human T lymphocytes.

In addition, due to the absence, in polyclonal antibodies according to the present invention, of the antigenic determinant selected in a group comprising (i) N-glycolneuraminic acid (Neu5Gc) and/or (ii) α-1,3-galactose, said polyclonal antibodies, when administered to a human organism, do not raise an immune response including production of anti-Neu5Gc or anti-GAL antibodies, which antibodies contributing to the occurrence of Immune Complexes (IC) and of IC related diseases such as serum sickness.

A method intended to identify or characterize polyclonal antibodies according to the present invention falls within the general knowledge of a man skilled in the art.

A method that may be used by the one skilled in the art for identifying or characterizing polyclonal antibodies according to the invention includes an Enzyme-linked immuno sorbent assay (ELISA) wherein anti-Neu5Gc antibodies and/or anti-Ga1 antibodies are used as detection molecules.

As anti-Neu5Gc antibodies for assessing the lack of Neu5Gc antigenic determinant, it may be cited the Gc-Free Basic Kit commercialized by the company Sialix, Inc.

As anti-Gal antibodies to demonstrate the lack of α-1,3-galactose antigenic determinant, may be considered the protocol disclosed in Jianq-Qiang Wang et al. (J. Am. Chem. Soc., 1999, 121: 8181) or those commercialized under the name WH0051083M1 Sigma by the company Sigma-Aldrich.

According to an ELISA method wherein specific anti-Neu5Gc and/or anti-Gal antibodies would be immobilized in wells of a microtiter plate, sole the antibodies which comprise the antigenic determinant selected in a group comprising (i) N-glycolneuraminic acid (Neu5Gc) and/or (ii) α-1, 3-galactose form a complex with the said anti-Neu5Gc and/or anti-Gal antibodies and thus, remain bound to the wells. When using such an ELISA method, polyclonal antibodies according to the invention are those which are devoid of one or more of the antigenic determinants selected in a group comprising (i) N-glycolneuraminic acid (Neu5Gc) and/or (ii) α-1,3-galactose, and are consequently those which do not form complexes with (i) anti-Neu5Gc antibodies, (ii) anti-Gal antibodies or (iii) both anti-Neu5Gc antibodies and anti-Gal antibodies.

This invention also relates to a method for producing a composition comprising polyclonal antibodies according to the invention comprising the steps of:

a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional α-(1,3)-galactosyltransferase;

b) immunizing the said genetically altered non-human mammal against human cells; and c) collecting the antibodies contained in a body fluid of the said genetically altered non-human mammal of step b), whereby a composition comprising polyclonal antibodies is obtained.

In some embodiments, the composition according to the invention may be prepared by mixing the polyclonal antibodies collected at step c) of the method described above, with one or more pharmaceutically acceptable excipients, such as a physiologically acceptable carrier, excipients or stabilizers.

In some embodiments, the polyclonal antibodies are purified before being used in a composition according to the invention.

In some embodiments, a composition of polyclonal antibodies according to the invention is in liquid form.

In some of the embodiments, a composition of polyclonal antibodies according to the invention is in a solid form, which includes a lyophilized form.

The composition of the invention may be formulated according to standard methods such as those described in Remington: The Science and Practice of Pharmacy (Lippincott Williams & Wilkins; Twenty first Edition, 2005).

Pharmaceutically acceptable excipients that may be used are, in particular, described in the Handbook of Pharmaceuticals Excipients, American Pharmaceutical Association (Pharmaceutical Press; 6th revised edition, 2009).

In order to treat a patient in need, such as above-mentioned, a therapeutically effective dose of the composition according to the invention may be administered.

By "therapeutically effective dose" herein is meant a dose that produces the effects for which it is administered. The exact dose will depend on the purpose of the treatment, and will be ascertainable by one skilled in the art using known techniques. Dosages may range from 0.001 to 100 mg of polyclonal antibodies according to the invention per kg of body weight (mg/kg) or greater, for example 0.1, 1.0, 10, or 50 mg/kg of body weight, with 1 to 10 mg/kg being preferred. The dosage and frequency of administration may be adapted depending of the host response as well as the frequency of injection owing to a better tolerance.

As is known in the art, adjustments for protein degradation, systemic versus localized delivery, as well as the age, body weight, general health, sex, diet, time of administration, drug interaction and the severity of the condition may be necessary, and is easily determined with routine experimentation by those skilled in the art.

Administration of the composition of the invention may be done in a variety of ways, including, but not limited to, orally, subcutaneously, intravenously, parenterally, intranasally, intraortically, intraocularly, rectally, vaginally, transdermally, topically (e.g., gels), intraperitoneally, intramuscularly, intrapulmonary or intrathecally.

The composition of the invention may be administered with other therapeutics concomitantly, i.e., the therapeutics described herein may be co-administered with other therapies or therapeutics, including for example, small molecules, other biologicals, radiation therapy, surgery, etc.

In a most preferred embodiment, a composition according to the invention is in a form suitable for administration by intravenous route.

According to a particular embodiment, a composition according to the invention may further comprises at least one immunosuppressive drug, such as glucocorticoids, cytostatics (Azathioprine, Methotrexate), antibodies, drugs acting on immunophilins (Cyclosporine, Tacrolimus, Rapamicin).

3. Method for Producing a Composition According to the Invention

As above-mentioned, a method for producing a composition according to the invention comprises the steps of:

a) providing a genetically altered non-human mammal lacking a first gene selected in a group comprising (i) a gene encoding a functional cytidine-5'-monophosphate N-acetyl neuraminic acid hydrolase (CMAH) and (ii) a gene encoding a functional α-(1,3)-galactosyltransferase;

b) immunizing the said genetically altered non-human mammal against human cells; and c) collecting the antibodies contained in a body fluid of the said genetically altered non-human mammal of step b).

According to a particular embodiment, the genetically altered non-human mammal may further lacks a second gene distinct from the first gene, the said second gene being selected from the group comprising (i) a gene encoding a functional cytidine-5'-monophosphate N-acetyl neuraminic acid hydrolase (CMAH) and (ii) a gene encoding a functional α-(1,3)-galactosyltransferase.

Preferably, the method of the invention may further comprises a step d) of purifying the said polyclonal antibodies from the said body fluid.

3.1. Step a) of Providing a Genetically Altered Non-Human Mammal

For preparing a composition according to the invention, it is performed a first step a) consisting of providing a genetically altered non-human transgenic mammal lacking a gene selected in a group comprising (i) a gene encoding a functional cytidine-5'-monophosphate N-acetyl neuraminic acid hydrolase (CMAH) and/or (ii) a gene encoding a functional α-(1,3)-galactosyltransferase.

Preferably, the said genetically altered non-human mammal is a CMAH and/or GGTA1 knockout non-human transgenic mammal (or CMAH and/or GGTA1 KO non-human mammal), which includes a CMAH and GGTA1 double-knockout non-human transgenic mammal.

As used herein, a "knockout non-human transgenic mammal" consists of a non-human transgenic mammal in which the function of one or more alleles of the considered gene has been altered, for example, by homologous recombination or other insertion or deletion.

In certain embodiments, this gene is disrupted. By "disrupted gene" is meant a portion of the genetic code has been altered, thereby affecting transcription and/or translation of that segment of the genetic code, e.g., rendering that segment of the code unreadable through knockout techniques or by insertion of an additional gene for a desired protein or insertion of a regulatory sequence that modulates transcription of an existing sequence.

In some embodiments of the invention, all of the cells of the non-human transgenic mammal include the disrupted gene.

In certain embodiments, the knockout non-human transgenic mammal is a non-human transgenic mammal in which one or more alleles of the considered gene has been rendered nonfunctional.

In some embodiments, both alleles of the considered gene are rendered non-functional. Such embodiments include those commonly referred to as "gene knockouts," "gene knock-ins" and any other modification of one or more native allele of the native considered gene that renders such gene non-functional. Such non-human transgenic mammal is useful as the source for producing a composition according to the present invention.

A method for obtaining a genetically altered non-human mammal lacking a gene selected in a group comprising (i) a gene encoding a functional cytidine-5'-monophosphate N-acetyl neuraminic acid hydrolase and/or (ii) a gene encoding a functional α-(1,3)-galactosyltransferase falls within the general knowledge of a man skilled in the art.

A genetically altered non-human mammal lacking the gene encoding a functional cytidine-5'-monophosphate N-acetyl neuraminic acid hydrolase is called CMAH KO non-human mammal.

A genetically altered non-human mammal lacking the gene encoding a functional α-(1,3)-galactosyltransferase is called GAL KO non-human mammal.

A method for obtaining a CMAH knockout non-human transgenic mammal is notably described in WO 2006/133356 which more particularly discloses a method for producing animal products devoid of N-glycomeuraminic acid (Neu5Gc) for human use comprising the steps of: preparing a genetically altered non-human mammal lacking a functional cytidine-5'-monophosphate N-acetyl neuraminic acid hydrolase (CMAH) gene; and extracting at least one animal product from the genetically altered non-human animal.

A method for obtaining a GAL knockout non-human transgenic mammal falls within the general knowledge of the man skilled in the art (Cooper D K et al., Genetically engineered pigs, Lancet 1993, 342: 682; Lai L et al., Science 2002, 295: 1089; Sachs D H et al., Current Opinion in Organ Transplantation, 2009, 14:148-153).

A method for obtaining a GAL knockout non-human transgenic mammal is notably described in U.S. Pat. No. 7,547,816.

According to a particular embodiment, to obtain a composition according to the present invention, that is to said which comprises polyclonal antibodies directed against human lymphocytes and human thymocytes, wherein the said polyclonal antibodies are devoid of an antigenic determinant selected in a group comprising (i) N-glycolneuraminic acid (Neu5Gc) and (ii) α-1,3-galactose, involves the implementation of a genetically altered non-human mammal lacking a gene selected in a group comprising (i) a gene encoding a functional cytidine-5'-monophosphate N-acetyl neuraminic acid hydrolase (CMAH) and (ii) a gene encoding a functional α-(1,3)-galactosyltransferase.

In other words, said specific genetically altered non-human mammal is a double CMAH and GAL knockout non-human transgenic mammal.

A protocol to obtain this specific CMAH and GAL double knockout non-human transgenic mammal is described in Lutz A L et al. (Xenotransplantation, 2013; 20 (1): 27-35) or in Conchon S. et al. (Xenotransplantation; special issue International Xenotransplantation Association IXA 2013, 2013, Vol. 20, Issue 5).

As genetically altered non-human transgenic mammal which may be used in the present invention, may be notably cited Ovidae, Bovidae, Suidae, Leporidae and Equidae.

Preferably, the genetically altered non-human transgenic mammal may consist of a pig.

Indeed, pigs are preferred for obtaining a composition according to the present invention, and more particularly an ALS or ATG, in that they are particularly interesting on an industrial point of view.

Indeed, pigs offer several advantages, notably compared to the rabbit, in that the volume of immune sera, and thus of polyclonal antibodies of interest, which may be collected is proportional to the animal's weight ratio (30 times better).

What is more, pigs do not need to be euthanized at sera harvesting time and thus, legal procedures allowing harvesting sera are significantly facilitated.

Indeed, 10% of animal blood volume per month may be collected.

For all these reasons, to obtain a composition according to the present invention from a genetically altered transgenic pig is particularly economic.

3.2. Step b) of Immunizing the Genetically Altered Non-Human Mammal Against Human Cells Once a genetically altered non-human transgenic mammal lacking a gene selected in a group comprising (i) a gene encoding a functional cytidine-5'-monophosphate N-acetyl neuraminic acid hydrolase (CMAH) and/or (ii) a gene encoding a functional α-(1,3)-galactosyltransferase is obtained, a solution comprising notably human cells is then injected.

Preferably, human cells human cells of step b) may be selected in a group comprising human lymphocytes, human thymocytes and human cancer cells, and more particularly human lymphocytes and human thymocytes.

For example, a method for obtaining a solution comprising notably human T cells falls within the general knowledge of a man skilled in the art (EP 1 778 836; EP 0 335 804).

According to a particular embodiment, the said human cells are clones of human T-cells such as those disclosed in EP 0 335 804.

This embodiment is advantageous in that it allows overcoming possible unwanted side effects associated with the presence, together with human cells, especially T lymphocytes, of various cellular contaminants, including neutrophils, monocytes, red blood cells and platelets, which may involve, by the immunized non-human mammal, to the formation of corresponding contaminating antibodies.

A protocol to obtain a good level of immunization of the non-human transgenic mammal with respect to T cells is notably described in EP 0 335 804.

A such protocol may notably consists to immunize animals, such as rabbits, horses or pigs, preferably pigs, with repeated administration, according to known methods, of human T cells.

For example, several administrations are performed, intravenously or subcutaneously, with or without adjuvant, of $10^6$ to $10^9$ cells each time, the administrations being spaced of at least a week. About a week after the last immunization, serum is collected from immunized animals and isolated according to known methods.

The genetically altered non-human transgenic mammal will produce antibodies against these human T cells, said specific antibodies being devoid of the antigenic determinant Neu5Gc and/or α-1,3-Gal according to the nature of the considered genetically altered non-human transgenic mammal.

3.3. Step c) of Collecting the Antibodies Contained in the Body Fluid of the Genetically Altered Non-Human Mammal of Step b).

Then, a portion of the blood fluid of said genetically altered non-human transgenic mammal is removed from which antibodies, whose antibodies of interest, are collected.

According to a particular embodiment, the said body fluid may be selected in a group comprising blood plasma and blood serum.

A protocol for obtaining a blood fluid, and more particularly a blood plasma or a blood serum, falls within the general knowledge of a man skilled in the art.

3.4. Optional Step d) of Purifying the Antibodies from the Body Fluid of Step c)

According to a preferred embodiment, and as above-mentioned, a method according to the invention may further comprise a step d) of purifying the antibodies from the said body fluid.

Said step d) of purifying is advantageous in that it notably allows overcoming possible unwanted side effects associated with the presence, within the body fluid, of various cellular contaminants which may involve, by the immunized non-human mammal, to the formation of corresponding contaminating antibodies.

Said step d) of purifying is also advantageous in that it allows obtaining composition having a desired degree of purity.

Said step d) of purifying falls within the general knowledge of a man skilled in the art. All possible adaptation of any conventional purifying protocol also falls within the general knowledge of a man skilled in the art. In this respect, according to a first variant, a composition according to the invention may be the anti-Lymphocyte Serum (ALS), the Anti-Thymocyte Globulin serum (ATG) or the Anti-cancer cells serum as such, preferably a composition according to the invention may be the anti-Lymphocyte Serum (ALS) or the Anti-Thymocyte Globulin serum (ATG) as such.

As an appropriate method for obtaining said ALS or ATG, may notably be cited the method of fractionated precipitation with ethanol, with ammonium sulfate, with rivanol or with polyethylene glycol, the method by passage through ion exchange columns. The antibodies obtained can be then subjected to conventional treatments for their intravenous administration, for example by enzymatic cleavage treatments plasmin, papain or pepsin.

In this regard, may be more particularly cited the protocol implemented in example 3 of EP 0 335 804, which implements an ion exchange chromatography on DEAE cellulose.

According to other embodiments, a composition according to the invention may consist of a composition wherein the antibodies obtained at step c) of the method described above are separated from other cellular substituents other than antibodies, including notably neutrophils, monocytes, red blood cells and platelets.

According to these other embodiments, a composition according to the invention may consist of a composition containing the purified polyclonal antibodies that are initially present in the serum, the said purified polyclonal antibodies being substantially free of protein components of the serum or even polyclonal antibodies that are substantially free of any substance that was initially contained in the serum used as the starting product.

As an appropriate method for purifying these polyclonal antibodies of interest, may be cited those methods for purifying antibodies with an affinity support onto which coupled to the antigen, on protein G or on protein A, for example those commercialized by the companies ProteoGenix, Cell Biolabs, Inc. or CliniSciences or still disclosed in EP 1 601 697, JP 7 155 194 or U.S. Pat. No. 6,870,034.

May also be cited an affinity support for the selective fixation of the antibodies of interest from a blood fluid, comprising a solid support material having immobilized aptamer which specifically binds said antibodies of interest from a blood fluid. A such method is notably disclosed in WO 2010/094,901.

4. Medical Uses According to the Invention

As above-mentioned, the present invention, according to one of its aspects, relates to the use of a genetically altered non-human mammal lacking a first gene selected from the group comprising (i) a gene encoding a functional cytidine-5'-monophosphate N-acetyl neuraminic acid hydrolase (CMAH) and (ii) a gene encoding a functional α-(1,3)-galactosyltransferase, for producing a composition comprising polyclonal antibodies directed against human cells.

According to a particular embodiment, this genetically altered non-human mammal may be further lacking a second gene distinct from the first gene, the said second gene being selected from the group comprising (i) a gene encoding a functional cytidine-5'-monophosphate N-acetyl neuraminic acid hydrolase (CMAH) and (ii) a gene encoding a functional α-(1,3)-galactosyltransferase.

In particular, the absence of anti-Neu5Gc antibodies in a sample may be assessed according to the dosage method described in Padler-Karavani V et al. (PLoS One. 2013; 8 (3): e58443).

Preferably, human cells may be selected in a group comprising human lymphocytes, human thymocytes and human cancer cells, and more particularly may be selected in a group comprising human lymphocytes and human thymocytes.

According to another particular embodiment, the composition of the present invention may be a serum directed against human cells, the said composition being preferably selected in a group comprising an anti-Lymphocyte Serum (ALS), an Anti-Thymocyte Globulin serum (ATG) and anti-cancer cells serum, the said composition being more preferably selected in a group comprising an anti-Lymphocyte Serum (ALS) and an Anti-Thymocyte Globulin serum (ATG).

This invention also relates to a composition comprising polyclonal antibodies as described throughout the present specification, for its use as a medicament.

The present invention pertains to a composition comprising polyclonal antibodies as described throughout the present specification, for its use for preventing and/or treating a disorder selected in a group comprising a graft rejection, aplastic anemia, a graft-versus-host disease, a severe autoimmune disease and a malignant cells related disease (or cancer cells related disease).

The present invention also concerns a composition comprising polyclonal antibodies as described throughout the present specification, for its use for preventing and/or treating a graft rejection, and especially a renal graft rejection.

The present invention also concerns a composition comprising polyclonal antibodies as described throughout the present specification, for its use for preventing post-transplant immune complex (IC) related diseases, in particular serum sickness, skin rashes or fever as compared to a conventional serum directed against human lymphocytes or human thymocytes.

In addition, the present invention also relates to a method for inducing an immunosuppression state in an individual in need thereof, the said method comprising a step of administering to the said individual a composition according to the present invention.

According to a particular embodiment, the said individual may be affected with aplastic anemia.

According to another particular embodiment, the said individual may be the recipient of an allogenic or of a xenogenic organ grafting.

According to another particular embodiment, a composition comprising polyclonal antibodies as described throughout the present specification may be administered to an individual in need thereof in combination with at least one immunosuppressive drug.

As such immunosuppressive drug may be notably cited glucocorticoid, cytostasis (Methotrexate, Azathioprine and mercaptopurine), drugs acting on immunophilins (Cyclosporin, Tacrolimus and Sirolimus), Fingolimod, Mycophenolic acid, TNF-α (tumor necrosis factor-alpha) binding proteins (infliximab (Remicade), etanercept (Enbrel), or adalimumab (Humira)).

As illustrative of this particular embodiment, may be cited Marsh J et al. (Blood. 1999 Apr. 1; 93 (7): 2191-5) or Delmonico F L et al. (Ann Surg. 1987 November; 206 (5): 649-54).

The present invention is further illustrated by, without on any way being limited to, the examples below.

EXAMPLE

In all herein after examples, the implemented pigs all have an unmodified diet.

Example 1

Protocol for Preparing an ALS and an ATG from a Double GAL/CMAH KO Pig

Preliminarily, the implemented double GAL/CMAH KO pig is the one disclosed in Lutz A L et al. (Xenotransplantation, 2013; 20 (1): 27-35) or the one disclosed in Conchon S. et al. (Xenotransplantation; special issue International Xenotransplantation Association IXA 2013, 2013, Vol. 20, Issue 5).

The human T lymphocytes immortalized cell line used in the assay is the Jurkat line which is available at the American Type Culture Collection under the reference number CRL2899 (that may be also termed "T-cells" in the example herein).

1) Protocol of Immunization of the Double GAL/CMAH KO Pig with Respect to Human Lymphocytes T Immunization of the double GAL/CMAH KO pig described in Lutz A L et al. (Xenotransplantation, 2013; 20 (1): 27-35) or in Conchon S. et al. (Xenotransplantation; special issue International Xenotransplantation Association IXA 2013, 2013, Vol. 20, Issue 5) by administration of $3.10^8$ T-cells.

Performing three intravenous injections on days 0, 14 and 21.

Optionally, administering intravenously 10 doses of BCG, or any type of adjuvant, at $10^7$-$10^8$ germes/10 doses at day 5.

Collecting the serum on day 28, by bleeding. Collecting about 100 ml of pig serum.

2) Protocol for Obtaining an ALS from the Double GAL/CMAH KO Pig

Subjecting the above-mentioned pig serum to a chromatography on Whatman cellulose DEAE and then performing an elution step with a disodium phosphate buffer 1.5 g/L, pH 8.

Purifying the obtained gamma-globulin solution by double precipitation with sodium sulphate at 180 g/L, then 170 g/L, pH 7. Redissolving the precipitate in a solution of 0.3 M glycine, pH 7, so as to obtain a volume equal to the starting volume.

Alternatively, the above-mentioned step of purification may be carried out using Protein A followed by ions exchange column.

Hema-adsorbing the solution twice on pellets of human red blood cells (volume of pellet for each adsorption substantially equal to the volume of crude serum) to reduce the rate of haemagglutinins. Precipitating again the solution with sodium sulfate to remove hemoglobin. Dissolving the precipitate in 0.3 M glycine buffer, diafiltered against a final solution of glycine 10 g/L, NaCl 2 g/L, mannitol 10 g/L. Adding proteins to 5 g/L, and then lyophilized.

Comments:

The obtained ALS from the double GAL/CMAH KO pig is particularly interesting in that it is significantly less immunogenic compared to a conventional ALS.

This ALS thus allows reducing immune complex (IC) related diseases that grafted patients may develop consecutively to an allograft or a xenograft. What is more, this ALS allows also reducing serum sickness which may further appear.

All these advantages necessarily improve the long term graft survival.

Example 2

Immune Reaction of Double GAL/CMAH KO Pigs Against Human T-Cells (or Human PBL)

The immunization of double knock-out pigs according to example 1 (wherein no BCG or any other type of adjuvant is considered) and their wild-type counterparts was performed by three successive injections of $30.10^6$ Jurkat cells in phosphate-buffered saline: a first sub-cutaneous injection at day 0 followed by two intravenous injections at day 14 and 28. Jurkat cells were cultured in Neu5Gc-free medium and compounds. Blood was sampled at day 35, and serum was used for further experiments or purification of IgGs.

The detection of human PBLs-specific antibodies in said serum was adapted from the protocol described in Poirier N et al., Journal of Surgical Research, 2007. Briefly, $2,5.10^5$ human peripheral blood mononuclear cells were incubated with different dilutions of immunized pig serum (from 1:5 to 1:5000), or no serum as negative control, for 30 minutes at 4° C. After washing in FACS buffer (PBS, 1% BSA, 0,1% azide), cells were incubated with FITC-labeled goat anti-pig IgG antibody (AbD Serotec, reference: AAI41F) at a dilution of 1:30, for 30 minutes at 4° C. Cells were washed three times before resuspending in FACS buffer and immediate analysis on a BD FACSCanto™ II.

Results are indicated as median fluorescence intensity in a same experiment, for serum sampled at day 35 of the immunization protocol.

Figure 4:
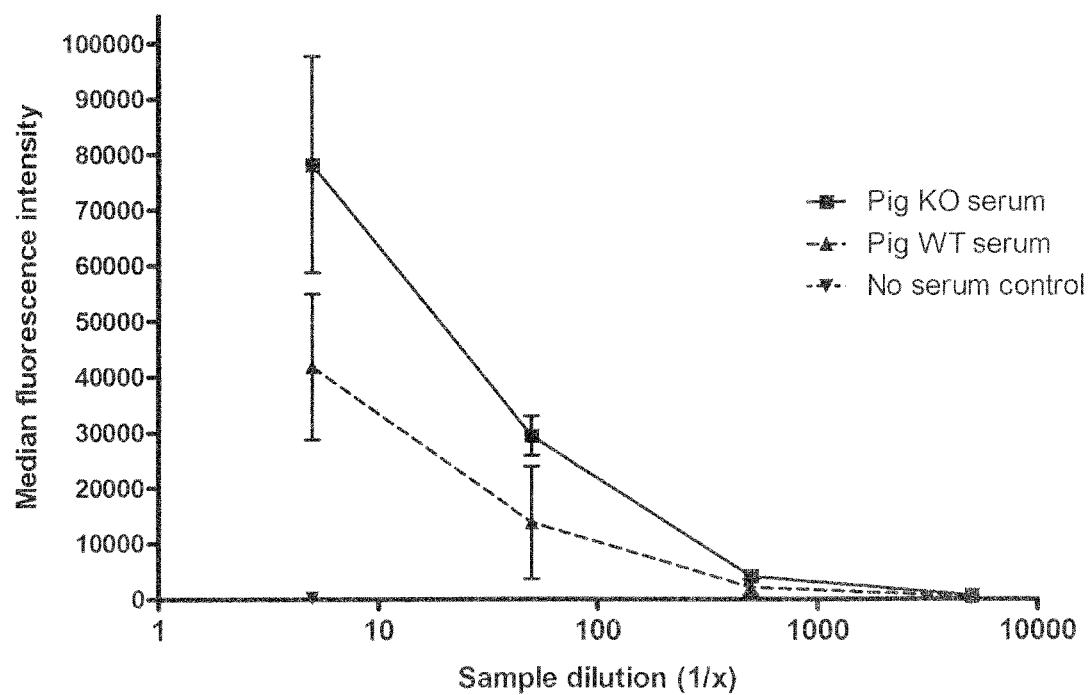
FIG. 4: illustrates a graph displaying amounts of anti human PBL-antibodies in the serum of immunized pigs by flow cytometry detection.

Results:

The results are displayed in FIG. 4. The stronger intensity is observed with the serum of double GAL/CMAH KO pigs. Thus, said double KO pigs mount a vigorous response against human PBLs (=Peripheral Blood Lymphocytes) following an immunization with Jurkat cells.

Example 3

Measure of Anti-Neu5Gc Antibodies (or Anti-Neu5Gc IgGs) in Double GAL/CMAH KO Pies Anti-Neu5Gc antibodies in immunized pig serum of example 2 (sampled at day 35 of the immunization protocol) were quantified using an ELISA assay adapted from Scobie et al., J Immunol., 2013, modified to improve specificity. Briefly, plates were coated with wild-type mouse serum (containing Neu5Gc) overnight at 4° C., then were blocked using PBS 1% ovalbumine 0,05% Tween for 2 hours at room temperature. During this time, samples were pre-incubated for 2 hours on ice with serum from CMAH-KO mice (no expression of Neu5Gc), and with or without 5 mM of synthetic Neu5Gc (for competitive absorption of anti-Neu5Gc antibodies). Samples were then added to the ELISA plate for 2 hours at room temperature. A horseradish peroxidase-labeled goat anti-pig IgG (Fc) secondary antibody (AbD Serotec, reference: AAI41P) was used for detection of anti-Neu5Gc antibodies, and plates were revealed using TMB substrate (Sigma-Aldrich). Optical density was read on a MRX plate reader (Dynatech Laboratories). Results are presented as the difference between the optical density of the wells inhibited or not inhibited by synthetic Neu5Gc.

Figure 5:
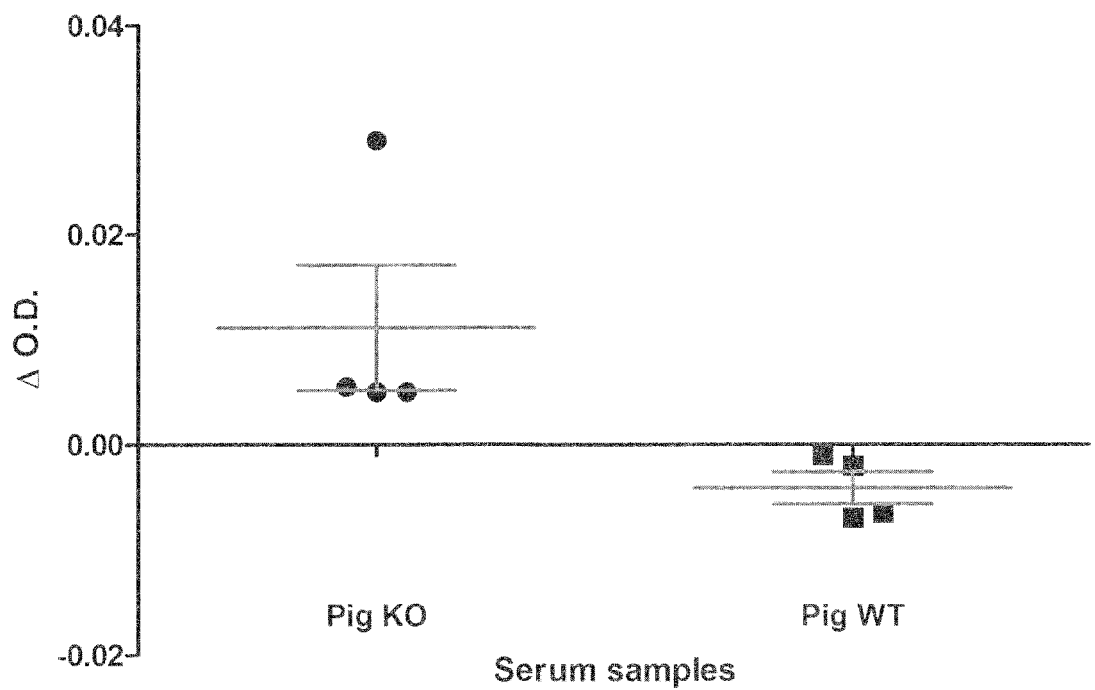
FIG. 5: illustrates a graph displaying an ELISA assay for the detection of anti-Neu5Gc IgGs in pigs serum.

Results:

The results are displayed in FIG. 5. Thus, double GAL/CMAH KO pigs only develop minimal amount of anti NeuGc antibodies, which shows that there will be no need for immune serum absorption.

Example 4

Link Between the Diagnostic of a Serum Sickness and the Kidney Graft Survival

This study assesses the proportion, among collected data from patients (mono-centric cohort of the DIVAT databank, Nantes Transplantation Institute, Nantes) having received a first kidney or kidney/pancreas graft and a treatment with ALS or ATG and in this regard having developed immune complex (IC) related diseases, who display a serum sickness and the related adverse effects with respect to the long term graft survival.

Figure 3:
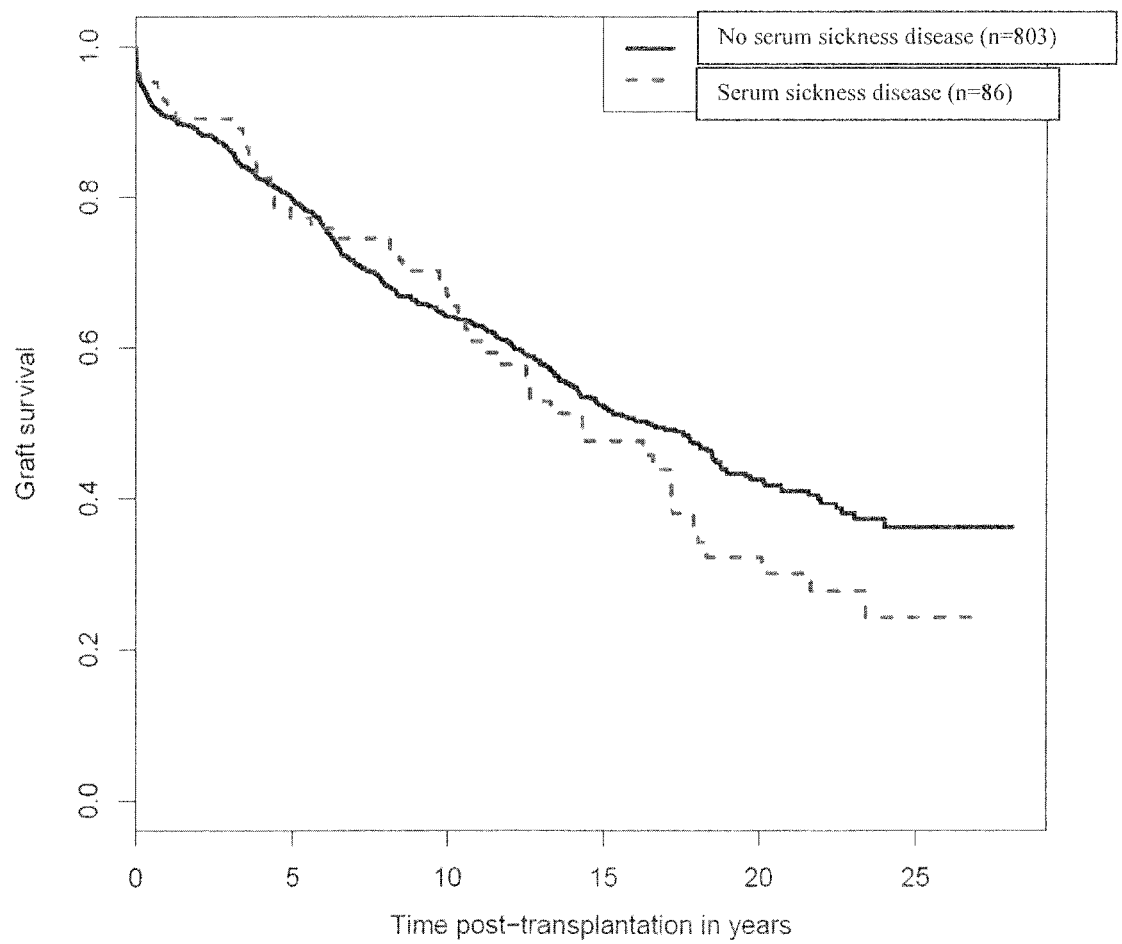
FIG. 3: illustrates a graph of collected data regarding, from patients (mono-centric cohort of the DIVAT databank, Nantes Transplantation Institute, Nantes) having received a first kidney or kidney/pancreas graft and a treatment with ALS or ATG and in this regard having developed immune complex (IC) related diseases, the proportion who display a serum sickness and the related adverse effects with respect to the long term graft survival (Abscissa: duration (in years); Ordinate: % of graft survival).

Said study is illustrated by FIG. 3 and by the three following tables A to C.

The table A displays characteristics of the patients forming the considered cohort. The tables B and C display the analyses of survival by univariate Cox and by multivariate Cox models respectively.

TABLE A

| Variables | Missing values Number (%) | Total (N = 889) Number (%) | Group with serum sickness (N = 86) Number (%) | Group without serum sickness (N = 803) Number (%) | p-value |
|---|---|---|---|---|---|
| RECEIVER | | | | | |
| Male | 0 (0.0) | 554 (62.3) | 55 (64.0) | 499 (62.1) | 0.8318 |
| Age ≥55 year | 0 (0.0) | 254 (28.6) | 9 (10.5) | 245 (30.5) | 0.0002* |
| Age ≥40 year | 0 (0.0) | 545 (61.3) | 42 (48.8) | 503 (62.6) | 0.0173* |
| BMI | 54 (6.1) | | | | 0.5115 |
| Thin | | 72 (8.6) | 10 (11.8) | 62 (8.3) | |
| Normal | | 724 (86.7) | 72 (84.7) | 652 (86.9) | |
| Obese | | 39 (4.7) | 3 (3.5) | 36 (4.8) | |
| Recurrent initial disease | 85 (9.6) | 301 (37.4) | 26 (32.1) | 275 (38.0) | 0.3545 |
| Pre-emptive dialysis | 35 (3.9) | 86 (10.1) | 13 (15.1) | 73 (9.5) | 0.1468 |
| PRA** anti class I | 65 (7.3) | 235 (28.5) | 23 (26.7) | 212 (28.7) | 0.7956 |
| PRA** anti class II | 391 (44.0) | 195 (39.2) | 30 (41.1) | 165 (38.8) | 0.8121 |
| History of diabetes | 0 (0.0) | 103 (11.6) | 9 (10.5) | 94 (11.7) | 0.8693 |
| History of HBP | 0 (0.0) | 613 (69.0) | 62 (72.1) | 551 (68.6) | 0.5896 |
| Cardiovascular history | 0 (0.0) | 127 (14.3) | 7 (8.1) | 120 (14.9) | 0.1207 |
| GRAFT | | | | | |
| Kidney-pancreas graft | 0 (0.0) | 96 (10.8) | 12 (14.0) | 84 (10.5) | 0.4185 |
| Year of graft | 0 (0.0) | | | | 0.0473* |
| 1985-1989 | | 351 (39.5) | 43 (50.0) | 308 (38.4) | |
| 1990-1999 | | 538 (60.5) | 43 (50.0) | 495 (61.6) | |
| Delayed graft | 21 (2.4) | 363 (41.8) | 36 (42.91) | 327 (41.7) | 0.9312 |

TABLE A-continued

| Variables | Missing values Number (%) | Total (N = 889) Number (%) | Group with serum sickness (N = 86) Number (%) | Group without serum sickness (N = 803) Number (%) | p-value |
|---|---|---|---|---|---|
| function (DGF) | | | | | |
| Cold ischemia ≥36 h | 12 (1.3) | 413 (47.1) | 44 (51.8) | 369 (46.6) | 0.4273 |
| Deceased donor | 0 (0.0) | 863 (97.1) | 83 (96.5) | 780 (97.1) | 0.7326 |
| Number of HLA mismatch | 2 (0.2) | 431 (48.6) | 35 (40.7) | 396 (49.4) | 0.1534 |
| DONOR | | | | | |
| Male | 1 (0.1) | 639 (71.9) | 67 (77.9) | 572 (71.2) | 0.2371 |
| Age ≥55 year | 0 (0.0) | 90 (10.1) | 4 (4.7) | 86 (10.7) | 0.1136 |
| Age ≥40 year | 0 (0.0) | 325 (36.6) | 21 (24.4) | 304 (37.9) | 0.0192* |
| Creatinine ≥133 µmol/l | 338 (38.0) | 98 (17.8) | 7 (15.2) | 91 (18.0) | 0.7837 |
| Vascular cause of death | 35 (3.9) | 266 (31.1) | 19 (7.1) | 247 (18.0) | 0.0982 |
| TREATMENT | | | | | |
| Corticoïdes | 0 (0.0) | 760 (85.5) | 79 (91.9) | 681 (84.8) | 0.1087 |

**PRA: Panel Reactive Antibody.

TABLE B

| Variable | Hazard Ratio (HR) | 95% CI | p |
|---|---|---|---|
| RECEIVER | | | |
| Sexe (Males/Females) | 1.38 | [1.12; 1.69] | 0.0021* |
| Age (≥55/<55) | 0.94 | [0.75; 1.18] | 0.6062 |
| BMI | | | 0.7158 |
| Thin/Normal | 0.98 | [0.69; 1.39] | 0.8940 |
| Obese/Normal | 1.21 | [0.75; 1.95] | 0.4270 |
| Recurrent initial disease (Yes/No) | 1.19 | [0.96; 1.48] | 0.1103* |
| Pre-emptive dialysis (Yes/No) | 0.81 | [0.58; 1.13] | 0.2222 |
| PRA** class I (Yes/No) | 1.34 | [1.08; 1.66] | 0.0082* |
| PRA** class II (Yes/No) | 1.33 | [1.04; 1.70] | 0.0229* |
| History of diabetes (Yes/No) | 0.82 | [0.59; 1.14] | 0.2278 |
| History of HBP (Yes/No) | 1.16 | [0.93; 1.45] | 0.1784* |
| Cardiovascular history (Yes/No) | 0.96 | [0.72; 1.26] | 0.7487 |
| Serum sickness (Yes/No) | | | 0.0233* |
| Before 10 years | 0.89 | [0.59; 1.35] | 0.5910 |
| After 10 years | 1.85 | [1.18; 2.91] | 0.0072* |
| Occurrence of rejection (Yes/No) | 2.62 | [2.14; 3.21] | <0.0001* |
| GRAFT | | | |
| Graft type (Kidney-pancreas/Kidney alone) | 0.80 | [0.56; 1.12] | 0.1900* |
| Year of graft (≥1990/<1990) | 0.82 | [0.67; 1.00] | 0.0462* |
| Delayed graft function (DGF) (Yes/No) | 1.33 | [1.09; 1.62] | 0.0055* |
| Cold ischemia (≥36 h/<36 h) | 1.16 | [0.95; 1.41] | 0.1356* |
| Donor-Receiver relation (Deceased donor/alive donor) | 1.04 | [0.62; 1.75] | 0.8705 |
| Number of HLA mismatch (≥4/<4) | 0.83 | [0.68; 1.01] | 0.0623* |
| DONOR | | | |
| Sexe (Males/Females) | 0.93 | [0.75; 1.15] | 0.5063 |
| Age (10 year) | 1.16 | [1.09; 1.25] | <0.0001* |
| Creatinine (≥133 µmol/l/<133 µmol/l) | 1.18 | [0.84; 1.66] | 0.3392 |
| Cause of death (Vascular/others) | 1.25 | [1.01; 1.55] | 0.0380* |
| TREATMENT | | | |
| Corticoïdes (Yes/No) | 0.34 | [0.27; 0.44] | <0.0001* |

*Univariate analysis. Significatives variables (p < 0.20),
**PRA: Panel Reactive Antibody.

TABLE C

| Variable | Hazard Ratio (HR) | 95% CI | p |
|---|---|---|---|
| Sexe of receiver (Males/Females) | 1.39 | [1.12; 1.73] | 0.0027* |
| Age of receiver (≥55/<55) | 1.03 | [0.805; 1.31] | 0.8427 |
| PRA** class I (Yes/No) | 1.51 | [1.20; 1.89] | 0.0004* |
| Serum sickness (Yes/No) | | | 0.0233* |
| Before 10 years | 0.90 | [0.59; 1.39] | 0.6430 |
| After 10 years | 1.72 | [1.08; 2.72] | 0.0218* |
| Occurrence of an acute rejection (Yes/No) | 2.86 | [2.29; 3.57] | <0.0001* |
| Year of graft (≥1990/<1990) | 1.06 | [0.84; 1.33] | 0.6278* |
| Cold ischemia (≥36 h/<36 h) | 1.25 | [1.02; 1.54] | 0.0322* |
| Number of HLA mismatch (≥4/<4) | 0.82 | [0.67; 1.01] | 0.0587* |
| Age (10 year) | 1.26 | [1.17; 1.36] | <0.0001* |
| Corticoïdes (Yes/No) | 0.26 | [0.20; 0.35] | <0.0001* |

*Multivariate analysis. Significatives variables (p < 0.05),
*PRA: Panel Reactive Antibody.

Comments:

Regarding these clinical data (see FIG. 3), the inventors shown that the serum sickness occurrence is an independent variable linked to the late graft loss.

Furthermore, the inventors shown that the relative risk ("HR" for "Hazard Ratio") regarding said serum sickness ranks number 2 after an acute rejection and stronger than all of the tested variables.

Finally, the inventors observed a statistical significant association between serum sickness and an increase in entire anti-Neu5Gc IgG antibodies years after transplantation.

The invention claimed is:

1. A composition comprising non-human mammal polyclonal antibodies from a non-human mammal directed against human cells, wherein the polyclonal antibodies are devoid of both (i) an N-glycolneuraminic acid (Neu5Gc) antigenic determinant and (ii) an α-1,3-galactose antigenic determinant.

2. The composition according to claim 1, wherein the human cells are selected from the group consisting of human lymphocytes, human thymocytes and human cancer cells.

3. The composition according claim 1, which is a serum directed against human cells.

4. The composition of claim 3, wherein the serum is selected from the group consisting of anti-Lymphocyte Serum (ALS), an Anti-Thymocyte Globulin serum (ATG) and an Anti-cancer cells Serum.

5. A method for producing a composition according to claim 1, comprising the steps of:
   a) providing a genetically altered non-human mammal lacking both (i) a gene encoding a functional cytidine-5'-monophosphate N-acetyl neuraminic acid hydrolase (CMAH) and (ii) a gene encoding a functional α-(1,3)-galactosyltransferase;
   b) immunizing the genetically altered non-human mammal against human cells; and then
   c) collecting antibodies contained in a body fluid of the genetically altered non-human mammal.

6. The method according to claim 5, wherein human cells of step b) are selected from the group consisting of human lymphocytes, human thymocytes and human cancer cells.

7. The method according to claim 5, wherein the body fluid is blood plasma or blood serum.

8. The method according to claim 5, wherein the non-human mammal is a pig.

\* \* \* \* \*